(12) United States Patent
Glasmachers

(10) Patent No.: US 10,585,055 B2
(45) Date of Patent: Mar. 10, 2020

(54) METHOD FOR OPERATING AN INDUCTIVE CONDUCTIVITY METER AND RESPECTIVE CONDUCTIVITY METER

(71) Applicant: KROHNE Messtechnik GmbH, Duisburg (DE)

(72) Inventor: Holger Glasmachers, Bochum (DE)

(73) Assignee: KROHNE MESSTECHNIK GMBH, Duisburg (DE)

( * ) Notice: Subject to any disclaimer, the term of this patent is extended or adjusted under 35 U.S.C. 154(b) by 21 days.

(21) Appl. No.: 15/916,356

(22) Filed: Mar. 9, 2018

(65) Prior Publication Data

US 2018/0259470 A1 Sep. 13, 2018

(30) Foreign Application Priority Data

Mar. 9, 2017 (DE) .................. 10 2017 104 994

(51) Int. Cl.
| | |
|---|---|
| *G01N 27/02* | (2006.01) |
| *G01N 27/08* | (2006.01) |
| *G01R 27/22* | (2006.01) |
| *G01R 27/26* | (2006.01) |
| *G01N 33/18* | (2006.01) |

(52) U.S. Cl.
CPC ......... *G01N 27/023* (2013.01); *G01N 27/025* (2013.01); *G01N 27/08* (2013.01); *G01R 27/22* (2013.01); *G01R 27/2611* (2013.01); *G01N 33/18* (2013.01)

(58) Field of Classification Search
CPC .... G01N 27/23; G01N 27/2611; G01N 27/25; G01N 27/22; G01N 27/08; G01N 33/18
See application file for complete search history.

(56) References Cited

U.S. PATENT DOCUMENTS

| | | | | |
|---|---|---|---|---|
| 5,341,102 A | * | 8/1994 | Akiyama | ............. G01N 27/023 324/202 |
| 5,581,037 A | * | 12/1996 | Kwun | .................... G01N 29/14 73/623 |
| 5,659,251 A | | 8/1997 | Wakamatsu | |
| 5,793,214 A | | 8/1998 | Wakamatsu | |
| 7,616,000 B2 | * | 11/2009 | Chu | ................... G01R 33/3614 324/318 |

(Continued)

*Primary Examiner* — Tung X Nguyen
*Assistant Examiner* — Dominic E Hawkins
(74) *Attorney, Agent, or Firm* — David S. Safran; Roberts Calderon Safran & Cole, P.C.

(57) ABSTRACT

A method for operating an inductive conductivity meter having a transmitting coil, a receiving coil and a terminating impedance device, the transmitting coil having a transmitting coil terminal, the receiving coil having a receiving coil terminal and the terminating impedance device having a terminating impedance, wherein the receiving coil is terminated with the terminating impedance device and wherein the transmitting coil and the receiving coil are inductively coupled with one another by an electrically conductive medium. To provide an improved accuracy of a determination of a conductivity of a medium a setpoint input impedance is specified, an input impedance is determined at the transmitting coil terminal, the terminating impedance is set such that the input impedance is matched to the setpoint input impedance, and a conductivity of the medium is determined using the adjusted input impedance and the set termination impedance.

9 Claims, 3 Drawing Sheets

(56) References Cited

U.S. PATENT DOCUMENTS

| | | | |
|---|---|---|---|
| 8,451,007 B2 | 5/2013 | Wang et al. | |
| 8,581,575 B2 | 11/2013 | Eberheim et al. | |
| 2009/0240435 A1* | 9/2009 | Itskovich | G01V 3/28 |
| | | | 702/7 |
| 2010/0171483 A1* | 7/2010 | Frost | G01N 17/006 |
| | | | 324/71.1 |
| 2010/0295558 A1* | 11/2010 | Eberheim | G01N 27/023 |
| | | | 324/654 |
| 2016/0041236 A1* | 2/2016 | Nakayama | G01R 33/0029 |
| | | | 324/239 |
| 2016/0043586 A1* | 2/2016 | Wang | H02J 7/0052 |
| | | | 320/107 |
| 2017/0149352 A1* | 5/2017 | Arisawa | H02M 7/06 |

\* cited by examiner

METHOD FOR OPERATING AN INDUCTIVE CONDUCTIVITY METER AND RESPECTIVE CONDUCTIVITY METER

BACKGROUND OF THE INVENTION

Field of the Invention

The invention relates to a method for operating an inductive conductivity meter. The inductive conductivity meter comprises a transmitting coil, a receiving coil and a terminating impedance device. Thereby, the transmitting coil has a transmitting coil terminal, the receiving coil has a receiving coil terminal, and the terminating impedance device has a terminating impedance. The receiving coil is terminated with the terminating impedance device and the transmitting coil and the receiving coil are inductively coupled with one another by an electrically conductive medium.

In addition, the invention relates to an inductive conductivity meter. The inductive conductivity meter also has a transmitting coil, a receiving coil, a terminating impedance device and, additionally, a control device. Thereby, the transmitting coil has a transmitting coil terminal, the receiving coil has a receiving coil terminal, and the terminating impedance device has a terminating impedance. The receiving coil is electrically terminated with the terminating impedance device. During operation, the transmitting coil and the receiving coil are inductively coupled with one another by an electrically conductive medium.

Description of Related Art

In contrast to conductive conductivity meters, inductive conductivity meters can also be used in aggressive and corrosive media such as industrial wastewater, seawater and acid solutions. This is possible because, in contrast to the electrodes of a conductive conductivity meter, both the transmitting coil and the receiving coil do not have to be in direct contact with a medium, but can be surrounded by a housing which is resistant to aggressive and corrosive media, without the functionality being impaired. Since there is no direct contact with aggressive and corrosive media in the presence of a housing, inductive conductivity meters are characterized by a long service life and are largely maintenance-free compared to conductive conductivity meters. With a housing, they are also suitable for hygienic applications in processes in the fields of food, beverage and pharmaceuticals.

A coil terminal of a coil such as the transmitting coil terminal of the transmitting coil or the receiving coil terminal of the receiving coil usually has two electrical terminals. In the transmitting coil, an electrical transmission alternating signal is fed into the transmitting coil via the electrical terminals of the transmitting coil terminal. The inductive coupling of the transmitting coil and the receiving coil with one another by the electrically conductive medium takes place in that the transmitting alternating signal fed into the transmitting coil generates eddy currents in the medium and the eddy currents induce an electrical receiving alternating signal in the receiving coil. The receiving alternating signal is measurable at the electrical terminals of the receiving coil terminal of the receiving coil in the form of a voltage or a current. Thus, a transmitting alternating signal causes a receiving alternating signal. An alternating signal such as the transmitting alternating signal or the receiving alternating signal is usually sinusoidal or rectangular over time.

The terminating impedance device also usually has two electrical terminals between which the terminating impedance arises. The terminating impedance is thus implemented by the terminating impedance device and, as such, is a property of the terminating impedance device.

The electrical termination of the receiving coil with the terminating impedance device is carried out by electrically connecting the electrical terminals of the receiving coil terminal to the electrical terminals of the terminating impedance device so that the terminating impedance device is electrically connected in parallel with the receiving coil.

It is known from the prior art to determine an electrical conductivity of a medium, which inductively couples the transmitting coil and the receiving coil, from the ratio of an amplitude of a receiving alternating signal and an amplitude of a transmitting alternating signal. In this case, the amplitude of the transmitting alternating signal is usually fixed and the amplitude of the receiving alternating signal is measured. However, a problem in determining an amplitude such as the amplitude of the receiving alternating signal is that the accuracy of the determination is not constant over the entire range of values that the amplitude can assume, which can lead to errors in the determination of the electrical conductivity of the medium.

SUMMARY OF THE INVENTION

Thus, the object of the invention is to provide a method for operating an inductive conductivity meter and an inductive conductivity meter, in which the accuracy of a determination of a conductivity of a medium is improved compared to the prior art.

According to a first teaching, the invention relates to a method for operating an inductive conductivity meter, in which the stated object is achieved. The method according to the invention is characterized first and foremost by the following process steps:

In a first method step, a setpoint input impedance is specified.

In a second method step, an input impedance is determined at the transmitting coil terminal.

In a third method step, the terminating impedance is adjusted such that the input impedance is matched to the setpoint input impedance.

In a fourth method step, a conductivity of the medium is then determined using the adjusted input impedance and the set terminating impedance.

According to the invention, the individual method steps are also carried out several times as required. This applies, in particular, to the second and third method steps when the input impedance is adapted to the setpoint input impedance by means of an iterative method by varying the terminating impedance.

The invention is based on the finding that the electrical conductivity of the medium, which inductively couples the transmitting coil and the receiving coil with one another, is a parameter both in the input impedance and in a transfer function which describes the transmission of electrical alternating signals between the transmitting coil terminal and the receiving coil terminal. If, for example, a given transmitting alternating signal is fed into the transmitting coil terminal of the transmitting coil and if the conductivity of the medium changes, the input impedance changes, on the one hand, and, on the other hand, the receiving alternating signal at the receiving coil terminal correspondingly changes. By adjusting the terminating impedance, which, like the conductivity, is also a parameter in both the input impedance and the transfer function, such that the input impedance is again matched to the setpoint input impedance, as before the change in conductivity, the effect on the input impedance due to the change in the electrical conductivity of the medium is compensated. Thus, information about the change in the conductivity of the medium is contained in the change in the terminating impedance. This makes it possible to determine the conductivity of the medium using the adjusted input impedance and the set terminating impedance.

An impedance, such as the setpoint input impedance, input impedance and terminating impedance, has a real part and/or an imaginary part. Both the real and the imaginary part of an impedance can be implemented with passive electrical components such as resistors, inductors and capacitors, wherein a characteristic of a resistor is a resistance, a characteristic of an inductor is an inductance and a characteristic of a capacitor is a capacitance. Thus, a resistance value contributes to the real part and capacitances and inductances contribute to the imaginary part of an impedance.

The input impedance at the transmitting coil terminal is determined, for example, in that an alternating signal in the form of a given transmitting alternating voltage with an amplitude is fed into the transmitting coil terminal, i.e. at the two electrical terminals, an amplitude of a transmitting alternating current through the transmitting coil terminal caused by the transmitting alternating voltage is measured, and the input impedance is determined from the given amplitude of the transmitting alternating voltage and the measured amplitude of the of the transmitting alternating current. Alternatively, the input impedance can also be determined, for example, in that an alternating signal in the form of a given transmitting alternating current with an amplitude is fed into the transmitting coil terminal, an amplitude of a transmitting alternating voltage across the transmitting coil terminal caused by the transmitting alternating current is measured, and the input impedance is determined from the given amplitude of the transmitting alternating current and the measured amplitude of the of the transmitting alternating voltage.

The conductivity is usually determined in that an electrical resistance of the medium between the transmitting and receiving coils is determined and then the conductivity of the medium is determined using the resistance value and a geometry of the medium between the transmitting and receiving coils.

The method according to the invention has the advantage over methods known from the prior art that the determination of the conductivity of the medium is more accurate. The higher accuracy results, in particular, in that a change in the input impedance is compensated for and not measured, as is known from the prior art. As a result, the range of values of the amplitudes to be measured is less than the range of values that the amplitudes to be measured known from the prior art assume, so that inaccuracies in the measurement of amplitudes are smaller. The technical effort to implement the method is comparable to the technical effort for implementing the method known from the prior art.

In an implementation of the method for operating the inductive conductivity meter, it is provided that the input impedance is adjusted to the setpoint input impedance in such a manner that a real part of the input impedance corresponds to a real part of the setpoint input impedance. Usually, the input impedance has a real part and an imaginary part. The conductivity of the medium contributes to the real part and inductances of the transmitting coil and the receiving coil contribute to the imaginary part. Thus, it is basically sufficient when the real part of the input impedance corresponds to the real part of the setpoint input impedance.

In a further implementation of the method, it is provided that the input impedance is adjusted to the setpoint input impedance such that the input impedance corresponds to the setpoint input impedance. Thus, not only does the real part of the input impedance correspond to the real part of the setpoint input impedance, but also the imaginary part of the input impedance corresponds to the imaginary part of the setpoint input impedance. On the one hand, if the real parts and, on the other hand, the imaginary parts correspond to one another, the accuracy of determining the conductivity of the medium is increased as compared with a method in which only the real parts correspond to one another. Two real parts or two imaginary parts correspond, in particular, to one another when they have the same value.

According to a second teaching, the invention also relates to an inductive conductivity meter in which the stated object is achieved. The inductive conductivity meter according to the invention is initially and essentially characterized in that a setpoint input impedance is stored in the control device, that the terminating impedance of the terminating impedance device is adjustable and that the control device is designed to determine an input impedance at the transmitting coil terminal, to set the terminating impedance in such a manner that the input impedance is matched to the setpoint input impedance and to determine a conductivity of the medium using the adjusted input impedance and the set termination impedance.

A design of the inductive conductivity meter according to the invention provides that the control device is designed to carry out one of the described methods. Furthermore, the control device is usually adapted to generate transmitting alternating signals and to feed them into the transmitting coil and to measure receiving alternating signals.

In a further design of the inductive conductivity meter, it is provided that the terminating impedance device has a current sensor for measuring a receiving coil current through the receiving coil terminal and a controlled voltage source for setting a receiving coil voltage across the receiving coil terminal. A controlled voltage source is a voltage source at which a voltage, such as the receiving coil voltage, of the voltage source is adjustable by a signal source. Further, the control device is designed to determine the receiving coil current with the current sensor and to adjust the receiving coil voltage with the controlled voltage source such that the terminating impedance is set. Thus, the terminating impedance device represents an active impedance.

In a further development of the preceding design, it is provided that the current sensor is a shunt resistor and the controlled voltage source has an operational amplifier for providing the receiving coil voltage. A shunt resistor is a low-resistance electrical resistor for measuring electrical currents. The operational amplifier has such external circuitry that it represents a voltage source.

In a further development of the above development, it is provided that the controlled voltage source has a signal generator for controlling the operational amplifier. Thus, the signal generator is the signal source that determines the receiving coil voltage provided by the operational amplifier.

In a further development of the above development, it is further provided that the signal generator is designed to generate a continuous-value signal or a pulse width modulated signal for controlling the operational amplifier.

The above design with the current sensor and the controlled voltage source, in particular in conjunction with the developments of this design, implements a cost-effective active terminating impedance device.

The explanations concerning the method for operating an inductive conductivity meter apply correspondingly to the inductive conductivity meter and vice versa.

In detail, a plurality of possibilities exists for designing and further developing the method according to the invention for operating an inductive conductivity meter and the inductive conductivity meter as will be apparent form the following description of a preferred embodiment in conjunction with the accompanying drawings.

DETAILED DESCRIPTION OF THE INVENTION

Figure 1:
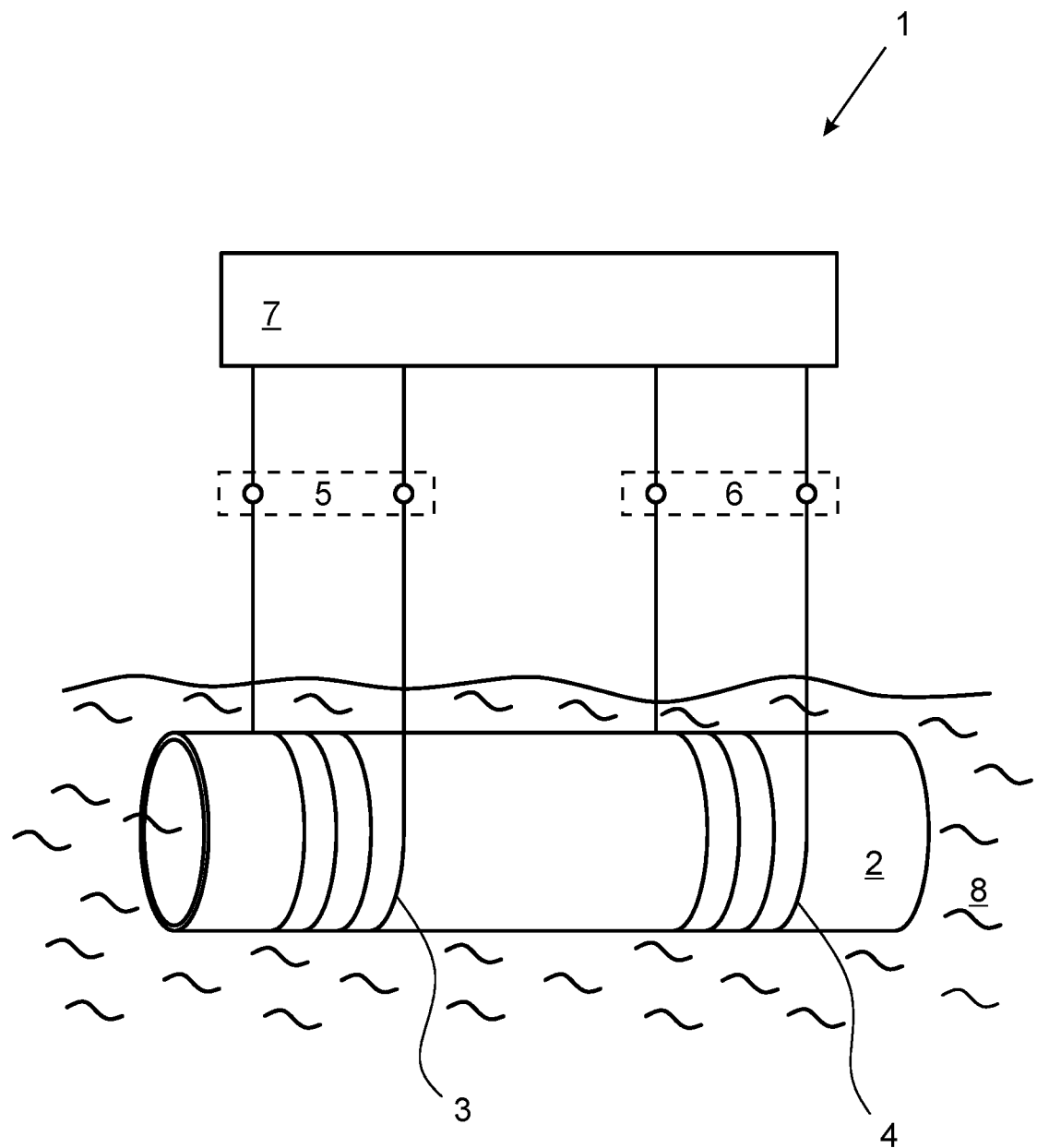
FIG. 1 shows an embodiment of an inductive conductivity meter.

FIG. 1 shows the inductive conductivity meter 1. The inductive conductivity meter 1 has the hollow-cylindrical carrier 2, on which the transmitting coil 3 and the receiving coil 4 are arranged. The transmitting coil 3 and the receiving coil 4 are arranged on the hollow cylindrical carrier 2 by being wound around the hollow cylindrical carrier 2, wherein the transmitting coil 3 has the number $N_1$ turns and the receiving coil 4 has the number $N_4$ turns. Furthermore, the transmitting coil 3 has the electrical transmitting coil terminal 5 and the receiving coil 4 has the electrical receiving coil terminal 6. The inductive conductivity meter 1 also has the control device 7, which is designed to control the transmitting coil 3 and the receiving coil 4, which is why the control device 7 is also electrically connected to the transmitting coil terminal 5 of the transmitting coil 3 and to the receiving coil terminal 6 of the receiving coil. In addition, a setpoint input impedance is stored in the control device 7.

The hollow cylindrical carrier 2 with the transmitting coil 3 and the receiving coil 4 is immersed in the medium 8 and the inductive conductivity meter 1 is in operation. The medium 8 surrounds the hollow cylindrical carrier 2 and is also present in its interior. The medium 8 is electrically conductive and thereby couples the transmitting coil 3 and the receiving coil 4 inductively with one another. Since it is an abstracted schematic representation of the inductive conductivity meter 1, a housing, which is usually present and prevents direct contact of the transmitting coil 3 and the receiving coil 4 with the medium 8, is not shown here. By avoiding contact of the transmitting coil 3 and the receiving coil 4 with the medium 8, it is possible to use the inductive conductivity meter 1, in contrast to conductive conductivity meters, in aggressive and corrosive media such as industrial wastewater, seawater and acid solutions, without the functionality of the inductive conductivity meter 1 being impaired. The housing also makes it suitable for hygienic applications in processes in the fields of food, beverage and pharmaceuticals.

Figure 2:
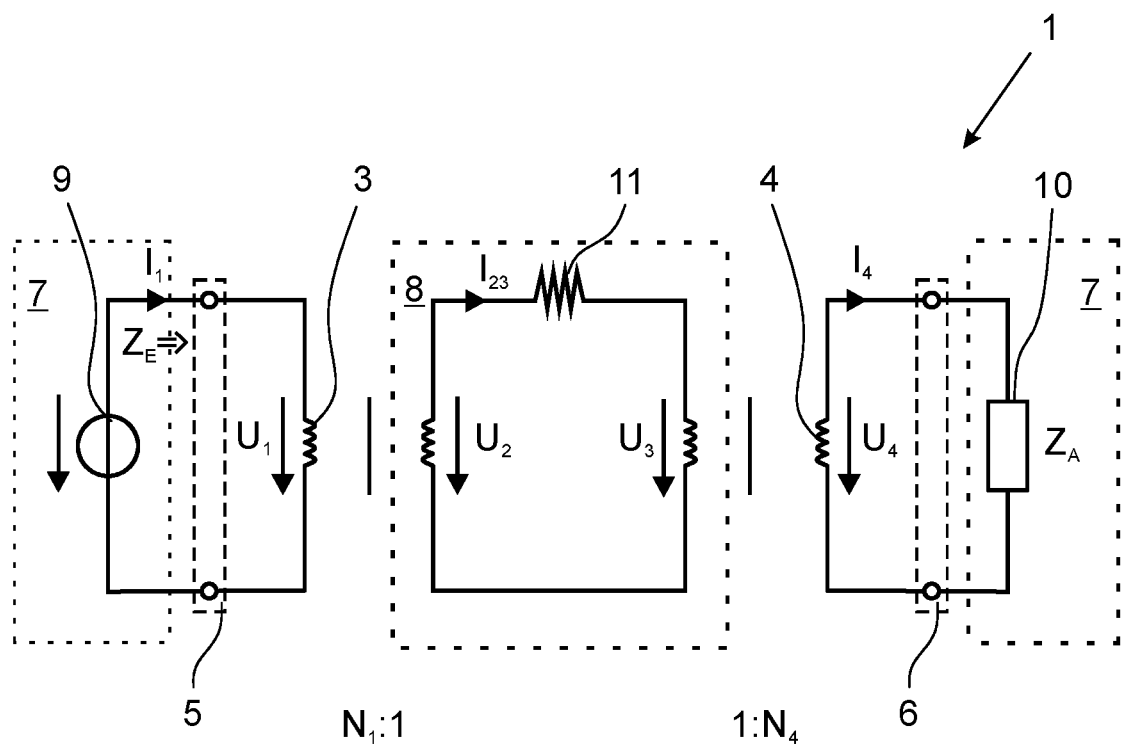
FIG. 2 is a partial electrical equivalent circuit diagram of the inductive conductivity meter from FIG. 1.

FIG. 2 shows a partial electrical equivalent circuit diagram, on the one hand, of the inductive conductivity meter 1 and, on the other hand, of the electrically conductive medium 8.

The equivalent circuit diagram of the inductive conductivity meter 1 has the transmitting coil 3, the transmitting coil terminal 5 and the transmitting alternating voltage source 9, wherein the transmitting alternating voltage source 9 is connected to the transmitting coil terminal 5 such that the transmitting alternating voltage source 9 and the transmitting coil 3 are electrically connected in parallel. Furthermore, the equivalent circuit of the inductive conductivity meter 1 has the receiving coil 4, the receiving coil terminal 6 and the terminating impedance device 10, which is part of the control device 7 in this embodiment. The terminating impedance device 10 is connected to the receiving coil terminal 6 such that the terminating impedance device 10 and the receiving coil 4 are electrically connected in parallel.

The equivalent circuit diagram of the electrically conductive medium 8 has the medium resistor 11 with the medium resistance $R_W$, which represents the electrical resistance of the medium 8 between the transmitting coil 3 and the receiving coil 4.

The transmitting alternating voltage source 9 is designed to generate a sinusoidal transmitting coil voltage $U_1$ given by the control device 7, and the control device 7 is designed to measure the transmitting coil current $I_1$. Thus, the transmitting coil voltage $U_1$ is a transmitting alternating voltage and the transmitting coil current $I_1$ is a transmitting alternating current. Due to the parallel connection of the transmitting alternating voltage source 9 and the transmitting coil 3, the transmitting coil voltage $U_1$ is also applied across the transmitting coil 3 and the transmitting coil current $I_1$ flows through the transmitting coil 3. Further, the control device 7 is designed to determine the input impedance $Z_E = U_1/I_1$ at the transmitting coil terminal 5 using the transmitting coil voltage $U_1$, which is usually measured by the control device 7, and the transmitting coil current $I_1$.

The inductive coupling of the transmitting coil 3 and the receiving coil 4 with one another by the electrically conductive medium 8 is given in that the transmitting alternating signal fed into the transmitting coil 3, which is characterized by the transmitting coil voltage $U_1$ and the transmitting coil current $I_1$, generates eddy currents in the medium 8 and the eddy currents induce a receiving alternating signal in the receiving coil 4, which is characterized by the receiving coil voltage $U_4$ and the receiving coil current $I_4$. The receiving coil voltage $U_4$ is incident across the receiving coil 4 and the receiving coil current $I_4$ flows through the receiving coil 4. Due to the parallel connection of the receiving coil 4 and terminating impedance device 10, the receiving coil voltage $U_4$ is also incident across the terminating impedance device 10 and the receiving coil current $I_4$ also flows through the terminating impedance device 10. The receiving coil voltage $U_4$ and the receiving coil current $I_4$ are specified by the terminating impedance $Z_A = U_4/I_4$. The generation of eddy currents in the medium 8 by the transmitting alternating signal takes place using a transformer coupling between the transmitting coil 3 and the medium 8 according to $U_1 = N_1 \cdot U_2$ and the transformer coupling between the medium 8 and the receiving coil 4 takes place according to $U_4 = U_3 \cdot N_4$.

Figure 3:
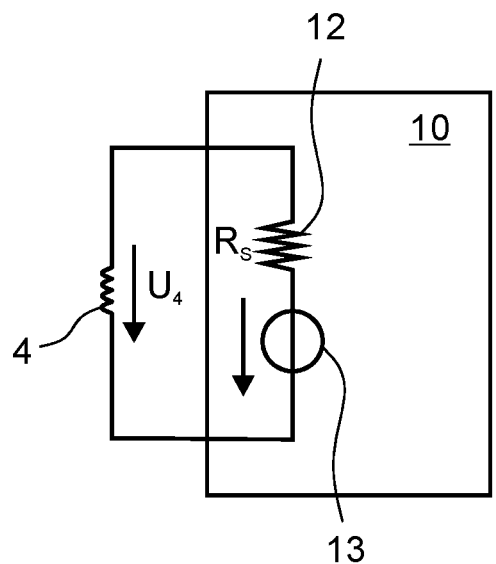
FIG. 3 is a partial electrical equivalent circuit diagram of the terminating impedance device from FIG. 2.
Figure 4:
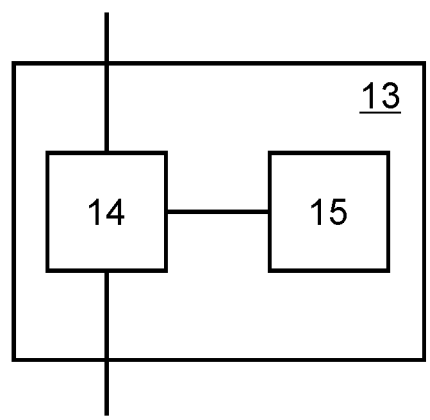
FIG. 4 is a partial electrical equivalent circuit diagram of the controlled voltage source from FIG. 3.

A partial equivalent electrical circuit diagram of the terminating impedance device 10 is shown in FIG. 3. The terminating impedance $Z_A$ of the terminating impedance device 10 is adjustable, and the control device 7 is designed to set the terminating impedance $Z_A$ of the terminating impedance device 10. Thus, the control device 7 controls the terminating impedance device 10. The terminating impedance device 10 has a current sensor 12 for measuring the receiving coil current $I_4$ through the receiving coil terminal 6 and a controlled voltage source 13 for adjusting the receiving coil voltage $U_4$ across the receiving coil terminal to set the terminating impedance. The control device 7 is designed to set the terminating impedance $Z_A$, to determine the receiving coil current $I_4$ with the current sensor 12 and to set the receiving coil voltage $U_4$ such that the terminating impedance $Z_A$ is set. Thus, an active terminating impedance $Z_A$ is implemented by the terminating impedance device 10 and the control device 7. In the present embodiment, the current sensor 12 is a shunt resistor and the controlled voltage source 13 has the operational amplifier 14 shown in FIG. 4 for providing the receiving coil voltage $U_4$ and the signal generator 15 for controlling the operational amplifier 14. In this case, the control device 7 is designed to control the signal generator 15. In the present embodiment, the signal generator 15 is designed to generate a continuous-value signal for controlling the operational amplifier 14.

A transfer function from the transmitting coil 3 to the receiving coil 4 is given by the following formula:

$$\frac{I_4}{U_1} = \frac{N_4}{N_1} \frac{1}{Z_A + R_W N_4^2 \left(1 + \frac{Z_A}{j\omega L_{44}}\right)}$$

The reciprocal of the input impedance $Z_E$, i.e., the input admittance $Y_E$, is given by the following formula:

$$Y_E = \frac{1}{N_1^2 R_W + \left(\frac{N_1}{N_4}\right)^2 (Z_A \| j\omega L_{44})} + \frac{1}{j\omega L_{11}}$$

In the above formulas, j is the imaginary unit, ω is the angular frequency, $L_{11}$ is an inductance between transmitting coil 3 and the medium 8, $L_{44}$ is an inductance between the receiving coil 4 and the medium 8, and ($Z_A \| j\omega L_{44}$) symbolizes a calculation instruction for calculating the impedance of a parallel connection of $Z_A$ and $j\omega L_{44}$.

Figure 5:
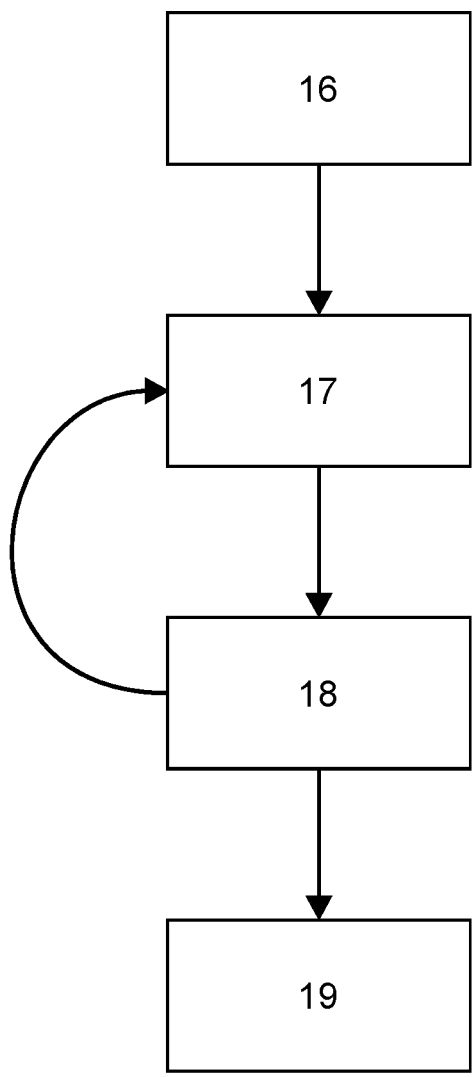
FIG. 5 is a flowchart of an example of a method for operating the inductive conductivity meter from FIG. 1.

It can be seen from the above formulas that the terminating impedance $Z_A$ is a parameter of both the transfer function and the input impedance $Z_E$. Thus, the input impedance $Z_E$ can be matched to the setpoint input impedance by adjusting the terminating impedance $Z_A$. For this, the control device 7 is designed for carrying out the method illustrated in the flowchart in FIG. 5 with the following method steps.

In the first method step 16, a setpoint input impedance is specified. This is the setpoint input impedance that is stored in the control device 7.

In the second method step 17, the input impedance $Z_E$ is determined at the transmitting coil terminal 5.

In the third method step 18, the terminating impedance $Z_A$ is adjusted such that the input impedance $Z_E$ is matched to the setpoint input impedance. In the fourth method step 19, a conductivity of the medium 8 is then determined using the adjusted input impedance $Z_E$ and the set terminating impedance $Z_A$. The conductivity is determined by first determining the medium resistance value $R_W$ and then the conductivity of the medium 8 using the medium resistance value $R_W$ and the geometry of the medium 8 between the transmitting coil 3 and the receiving coil 4.

The listed method steps are also carried out several times by the control device 7 as required. This applies, in particular, to the second method step 17 and the third method step 18 when the input impedance $Z_E$ is adapted to the setpoint input impedance by means of an iterative method by varying the terminating impedance $Z_A$.

What is claimed is:

1. A method for operating an inductive conductivity meter having a transmitting coil, a receiving coil and a terminating impedance device, wherein the transmitting coil has a transmitting coil terminal, the receiving coil has a receiving coil terminal and the terminating impedance device has a terminating impedance, wherein the receiving coil is terminated with the terminating impedance device and wherein the transmitting coil and the receiving coil are inductively coupled with one another by an electrically conductive medium, the method comprising the following steps:
specifying a setpoint input impedance,
determining an input impedance at the transmitting coil terminal,
setting the terminating impedance such that the input impedance is matched to the setpoint input impedance, and
determining a conductivity of the medium using the matched input impedance and the set termination impedance.

2. The method according to claim 1, wherein the matching of the input impedance to the setpoint input impedance is performed in a manner such that a real part of the input impedance corresponds to a real part of the setpoint input impedance.

3. The method according to claim 1, wherein the input impedance is adjusted to the setpoint input impedance such that the input impedance corresponds to the setpoint input impedance.

4. An inductive conductivity meter, comprising:
a transmitting coil,
a receiving coil,
a terminating impedance device, and
a control device,
wherein the transmitting coil has a transmitting coil terminal, the receiving coil has a receiving coil terminal and the terminating impedance device has a terminating impedance,
wherein the receiving coil is terminated with the terminating impedance device and
wherein, during operation, the transmitting coil and the receiving coil are inductively coupled with one another by an electrically conductive medium,
wherein a setpoint input impedance is stored in the control device,
wherein the terminating impedance of the terminating impedance device is adjustable, and
wherein the control device has means for determining an input impedance at the transmitting coil terminal, for setting the terminating impedance such that the input impedance is matched to the setpoint input impedance, and for determining a conductivity of the medium using the adjusted input impedance and the set terminating impedance.

5. The inductive conductivity meter according to claim 1, wherein the terminating impedance device is adapted to adjust the input impedance to the setpoint input impedance such that a real part of the input impedance corresponds to a real part of the setpoint input impedance.

6. The inductive conductivity meter according to claim 4, wherein the terminating impedance device has a current sensor for measuring a receiving coil current through the receiving coil terminal, and a controlled voltage source for setting a receiving coil voltage across the receiving coil terminal, and wherein the control device has means for determining the receiving coil current with the current sensor and to set the receiving coil voltage such that the terminating impedance is set.

7. The inductive conductivity meter according to claim 6, wherein the current sensor is a shunt resistor and the controlled voltage source has an operational amplifier for providing the receiving coil voltage.

8. The inductive conductivity meter according to claim 7, wherein the controlled voltage source has a signal generator for controlling the operational amplifier.

9. The inductive conductivity meter according to claim 8, wherein the signal generator has means for generating a continuous-value signal or a pulse width modulated signal for controlling the operational amplifier.

\* \* \* \* \*